(12) United States Patent
Bloom

(10) Patent No.: US 11,731,354 B2
(45) Date of Patent: Aug. 22, 2023

(54) APPARATUS, SYSTEM, AND METHOD FOR CREATING PROSTHETICS

(71) Applicant: Medico Supplies, Inc., Surrey (CA)

(72) Inventor: Terrance Bloom, Vancouver (CA)

(73) Assignee: Medico Supplies, Inc., Surrey (CA)

( * ) Notice: Subject to any disclaimer, the term of this patent is extended or adjusted under 35 U.S.C. 154(b) by 42 days.

(21) Appl. No.: 17/330,214

(22) Filed: May 25, 2021

(65) Prior Publication Data

US 2021/0362415 A1    Nov. 25, 2021

Related U.S. Application Data

(60) Provisional application No. 63/029,594, filed on May 25, 2020.

(51) Int. Cl.

| | | |
|---|---|---|
| *B29C 64/232* | (2017.01) | |
| *B33Y 80/00* | (2015.01) | |
| *A61F 2/50* | (2006.01) | |
| *B29C 64/236* | (2017.01) | |
| *B29C 64/241* | (2017.01) | |
| *B29C 64/245* | (2017.01) | |
| *B29C 64/255* | (2017.01) | |
| *B29C 64/295* | (2017.01) | |

(Continued)

(52) U.S. Cl.
CPC .......... *B29C 64/232* (2017.08); *A61F 2/5046* (2013.01); *B29C 64/209* (2017.08); *B29C 64/236* (2017.08); *B29C 64/241* (2017.08); *B29C 64/245* (2017.08); *B29C 64/255* (2017.08); *B29C 64/295* (2017.08); *B29C 64/314* (2017.08); *B29C 64/329* (2017.08); *B33Y 30/00* (2014.12); *B33Y 40/10* (2020.01); *B29L 2031/7532* (2013.01); *B33Y 80/00* (2014.12)

(58) Field of Classification Search
CPC ..... B29C 64/232; B29C 64/314; B33Y 30/00; A61F 2/5046
See application file for complete search history.

(56) References Cited

U.S. PATENT DOCUMENTS

| | | | |
|---|---|---|---|
| 2004/0231594 A1* | 11/2004 | Edwards | ............... B25B 11/005 118/719 |
| 2008/0159798 A1* | 7/2008 | Culp | ...................... G06K 1/121 235/375 |

(Continued)

*Primary Examiner* — Joseph S Del Sole
*Assistant Examiner* — John Robitaille
(74) *Attorney, Agent, or Firm* — Bochner PLLC; Andrew D. Bochner

(57) ABSTRACT

A system and a method for creating prosthetics using a prosthetic machine are disclosed. The method includes creating a three dimensional (3D) shape of a prosthetic using a software. Successively, the 3D shape is sent for printing based at least on an availability of a printer. The printing is achieved by taking the 3D shape and slicing into very thin horizontal slices and thereafter placing a slice upon a slice for the 3D shape. Further, granular polycarbonate material is placed in a cartridge at the top of a compression head. Further, granules are fed through a four stage heating and compression process. Further, a heated plastic is pressurized and forced through an extruder to extrude in a 1 mm×4 mm ribbon. Thereafter, a printed object is formed on a base plate through motion that is controlled by a plurality of linear axes and a rotary axis.

15 Claims, 12 Drawing Sheets

(51) Int. Cl.
  *B29C 64/314* (2017.01)
  *B29C 64/209* (2017.01)
  *B33Y 30/00* (2015.01)
  *B33Y 40/10* (2020.01)
  *B29C 64/329* (2017.01)
  *B29L 31/00* (2006.01)

(56) References Cited

U.S. PATENT DOCUMENTS

2013/0064707 A1* 3/2013 Matsui ................. B29C 64/176
  264/109
2016/0096321 A1* 4/2016 Fry ....................... B29C 64/106
  425/375
2018/0099453 A1* 4/2018 Cambron ............... B33Y 30/00

* cited by examiner

APPARATUS, SYSTEM, AND METHOD FOR CREATING PROSTHETICS

CLAIM OF PRIORITY

This application claims priority from U.S. Provisional Patent Application No. 63/029,594, filed on May 25, 2020, the contents of which are incorporated herein by reference.

FIELD OF THE DISCLOSURE

The present disclosure is generally related to additive manufacturing, and more particularly, to an apparatus, system, and method for creating prosthetics using a prosthetic machine.

BACKGROUND

Prosthetics are artificially manufactured body parts for corresponding biological body parts that may have been lost due to disease, injury, or deformation. Each individual's deformation may have different requirements, requiring different prosthetics to be designed and manufactured. For example, a prosthetic limb is manufactured for an amputee to allow users to be nearly as mobile as before the loss of the limb. Further, lower limbs prosthetics are designed to provide independence to the amputee from a wheelchair. Similarly, hand prosthetics are designed and manufactured to provide hand mobility.

Currently, medical expenses of prosthetics are very high, since each prosthetic is uniquely designed and manufactured. These burdensome expenses prevent a large population from accessing the prosthetics that would otherwise increase their mobility and independence. Further, the manufacturing of prosthetics is a slow and arduous process, material intensive, and is often somewhat inaccurate, producing inconsistent results. Moreover, there is difficulty in maintaining a consistent wall diameter along prosthetics. Therefore, there is a need for an improved system and method for creating prosthetics that could overcome the aforementioned issues. It would further be desirable to have an improved system and method for creating prosthetics with consistent thickness.

SUMMARY OF THE INVENTION

The invention of the present disclosure may be an additive manufacturing apparatus comprising a cartridge configured to accept a material and an extruder configured to extrude the material. The apparatus may also include a z-axis plate attached to the cartridge and the extruder and a z-axis motor configured to move the z-axis plate in a z-axis. In an embodiment, a main plate having a plate holder is configured to accept a build plate, where the build plate is configured to accept the material from the extruder. In an embodiment, the apparatus has a y-axis motor configured to move the main plate in a y-axis and a rotary motor configured to move the plate holder in a rotary axis. The apparatus may further include a computing device having a processor and a memory. The computing device may be in electrical communication with at least the z-axis motor, the y-axis motor, and the rotary motor, where the memory contains a design and a computer-readable instruction for printing the design, and where the computing device is configured to drive the z-axis motor, the y-axis motor, and the rotary motor in accordance with the computer-readable instruction for printing the design.

In an embodiment, the apparatus further comprises one or more fans disposed proximate to the extruder. The apparatus may comprise a carousel and a carousel arm configured to move the build plate between the carousel and the plate holder. In an embodiment, one or more heaters may be partially disposed within the plate holder. Further, an electromagnet may be partially disposed within the plate holder. In an embodiment, the apparatus includes an electromagnet adapter and a spindle, where the electromagnet and the spindle are disposed between the rotary motor and the plate holder. In another embodiment, the apparatus comprises one or more pulleys disposed on a main base, wherein the one or more pulleys enable rotational motion of the carousel. The apparatus may further comprise one or more pulley motors in mechanical communication with the one or more pulleys. In an embodiment, a hall sensor is disposed on the main plate.

In an embodiment, the apparatus may further comprise a z-axis screw in mechanical rotational communication with the z-axis motor, where the z-axis screw is at least partially threaded, and where the z-axis plate comprises a z-axis screw hole having a z-axis thread pattern configured to accept the z-axis screw. Further, the apparatus may comprise a y-axis screw in mechanical rotational communication with the y-axis motor, where the y-axis screw is at least partially threaded, and where the y-axis plate comprises a y-axis screw hole having a y-axis thread pattern configured to accept the y-axis screw. In an embodiment, the apparatus may further comprise one or more y-axis rails disposed between the y-axis plate and an end plate, wherein the main plate is slidably attached to the one or more y-axis rails.

In an embodiment, the apparatus may further comprise an x-axis motor configured to move the end plate in an x-axis, where the main plate is configured to move in the x-axis contemporaneously with the end plate. The apparatus may also comprise an x-axis screw in mechanical rotational communication with the x-axis motor, where the x-axis screw is at least partially threaded, and where the end plate comprises a x-axis screw hole having a x-axis thread pattern configured to accept the x-axis screw.

In an embodiment, the apparatus includes a front window disposed on the cartridge. In an embodiment, the feed motor and the gearbox may be configured to move the material from the cartridge to the extruder. Further, the extruder may be configured to extrude the material in a ribbon.

BRIEF DESCRIPTION OF THE DRAWINGS

The accompanying drawings illustrate various embodiments of systems, methods, and embodiments of various other aspects of the disclosure. Any person with ordinary skills in the art will appreciate that the illustrated element boundaries (e.g. boxes, groups of boxes, or other shapes) in the figures represent one example of the boundaries. It may be that in some examples one element may be designed as multiple elements or that multiple elements may be designed as one element. In some examples, an element shown as an internal component of one element may be implemented as an external component in another, and vice versa. Furthermore, elements may not be drawn to scale. Non-limiting and non-exhaustive descriptions are described with reference to the following drawings. The components in the figures are not necessarily to scale, emphasis instead being placed upon illustrating principles.

DETAILED DESCRIPTION

Embodiments of the present disclosure will be described more fully hereinafter with reference to the accompanying drawings in which like numerals represent like elements throughout the several figures, and in which example embodiments are shown. Embodiments of the claims may, however, be embodied in many different forms and should not be construed as limited to the embodiments set forth herein. The examples set forth herein are non-limiting examples and are merely examples among other possible examples.

Figure 1:
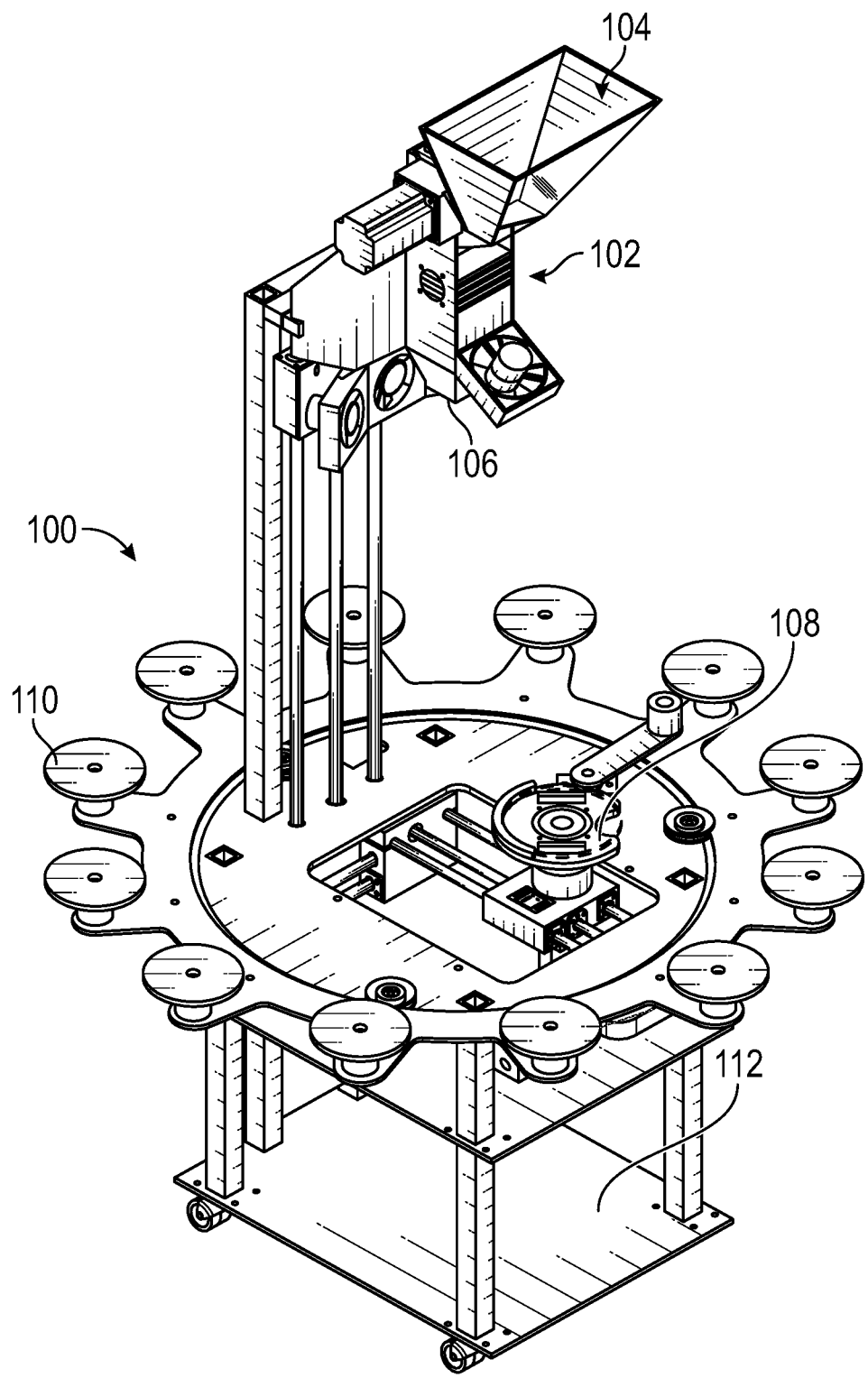
FIG. 1 illustrates a top side front perspective view of a machine for creating prosthetics, according to an embodiment.

FIG. 1 illustrates a machine 100 for creating prosthetics. The machine 100 may be referred to as a prosthetic machine. The machine 100 may be connected to a computing device having a design software. The design software may be used to design a three dimensional (3D) shape of the prosthetic. The computing device may encompass mobile devices, one or more servers, network services, micro-computers, or desktop computers. The computing device may include a processor for controlling the operation of the machine and its components. The computing device may also include RAM, ROM, an input/output module, and a memory. The processor may execute all software on the computing device. The software itself may be stored on the memory. The memory may be any suitable permanent storage technology, such as a hard drive. The memory may store the operating system and any software necessary for the functionality of the machine 100. The software and/or instructions stored on the memory, when executed by the processor, may perform various functions. The input/output connectivity may enable connectivity to a microphone, keyboard, touch screen, stylus, monitor, speaker, or any other component of the machine 100 (for example, any of the motors utilized by the machine 100).

In an embodiment, the computing device operates with a networked environment. For example, enabling communication with one or more remote computers. The computing device may be in communication with any number of servers. In an embodiment, the computing device is in communication with a power supply and is configured to appropriately route power to the various components of the machine 100.

The machine 100 may include a compression head 102 with a cartridge 104. The cartridge 104 may be coupled at a top of the compression head 102 and filled with a printing material. Further, the cartridge 104 may be coupled to an extruder (i.e., a custom shaped tip) 106 for extruding the printing material to form a printed object on a build plate (not shown). The build plate may be placed on a build plate assembly 108. Additionally, motion of the build plate may be controlled by a plurality of linear axes and a rotary axis. In one case, the plurality of linear axes may be three. In another case, the plurality of linear axes may be two. Further, the build plate may be placed on an outer carousel 110 after the printing of the printed object. Thereafter, the outer carousel 110 may be rotated to obtain the printed object and a new build plate may be retrieved and placed on the build plate assembly 108 for the next print.

Figure 2:
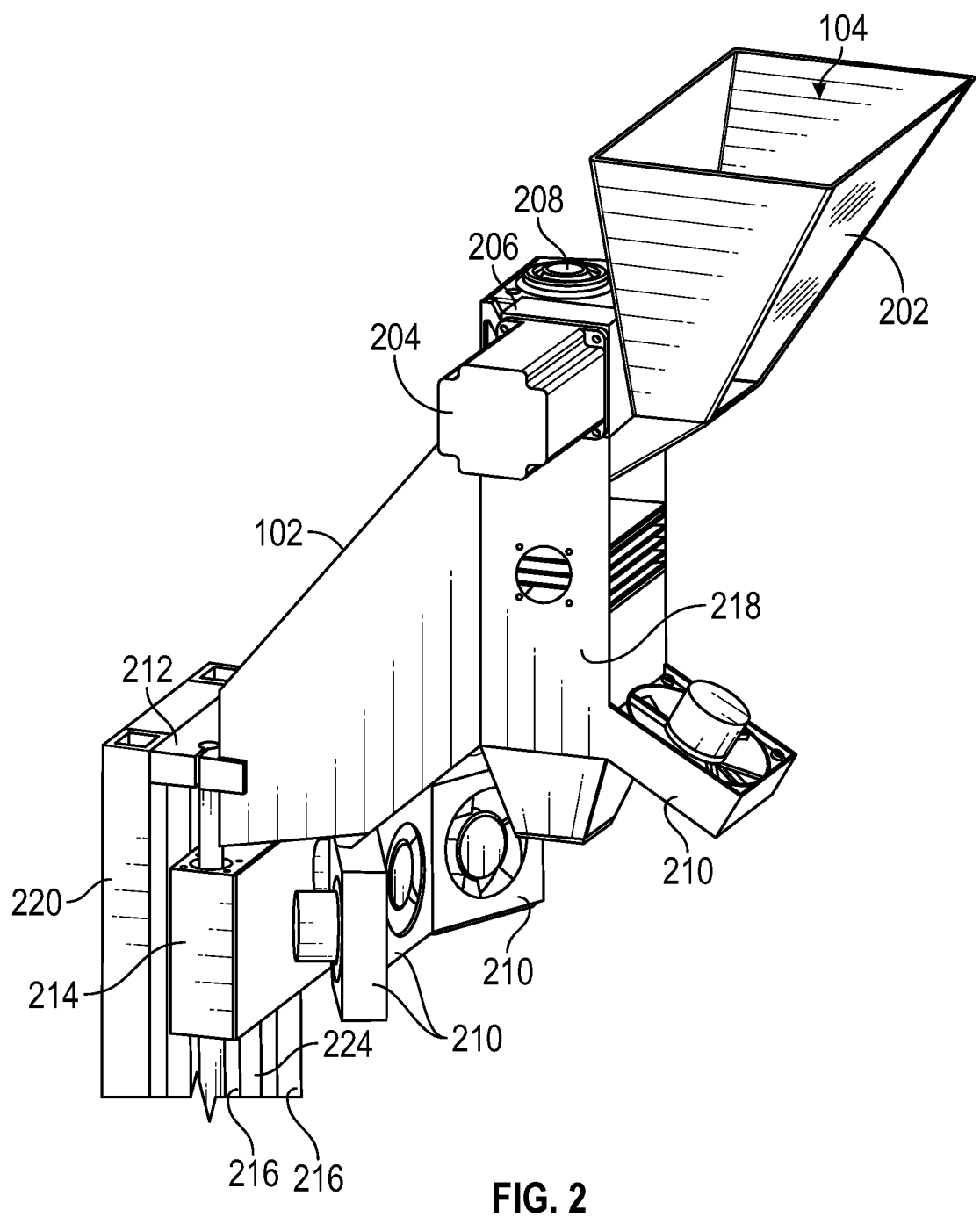
FIG. 2 illustrates a top side front perspective view of the machine showing a compression head and a cartridge, according to an embodiment.

At first, the 3D shape of a prosthetic may be created using a software. Successively, the 3D shape may be sent for printing based at least on an availability of a printer. It should be noted that the 3D shape may be queued for printing. In such an embodiment, the queued printing projects may be associated with one or more of the build plates on the carousel 110. The printing may be achieved by taking the 3D shape for printing and slicing it into very thin horizontal slices and thereafter placing a slice upon a slice for the 3D shape. In an embodiment, the thickness of the slice may be controlled by a rate of extrusion. Additionally, in order to produce an extrusion path, the 3D shape may be sliced horizontally at a specified pitch, for example, every 1 mm. Successively, granular polycarbonate material may be placed in the cartridge 104 at the top of the compression head 102, as shown in FIG. 2. Successively, granules may be fed through a multiple stage heating and compressing process. In one case, a four-stage heating and compression process may be performed to form heated plastic. The heated plastic may be pressurized and forced through the extruder i.e. the custom shaped tip 106 to extrude in a 1 mm×4 mm "ribbon". However, in alternate embodiments, the custom shaped extruder tip 106 may be configured to create any dimension, shape, or size, of material.

In an embodiment, the machine 100 includes a table component 112. The table component 112 may include one or more shelves and/or one or more legs. The table component 112 may offer additional storage (for example, storage for completed prosthetics and/or raw materials). In an embodiment, the table component 112 includes four legs and supports the weight of the machine 100. In an embodiment, the one or more legs may include wheels and or jacks. The wheels may enable movement of the machine 100 and the jacks may be configured to raise one or more legs to level the machine 100.

Referring to FIG. 2, the cartridge 104 may include a front window 202. In alternate embodiments, a window may be placed along any portion of the cartridge 104. However, in an alternate embodiment, the cartridge 104 is uniformly opaque. In an embodiment, a feed motor 204 is disposed atop a chute 218. The chute 218 may be configured to facilitate solid and/or fluid communication between the container 104 and the extruder 106. The feed motor 204 may be connected to a feed motor mount 206, where the feed motor mount 206 is connected to a gearbox 208. The gearbox 208 and/or feed motor 204 may be configured to drive material from the cartridge 104 to the extruder 106 (for example, through the chute 218). The chute 218 (or another component of the compression head 102) may be fitted with mechanisms for pressurizing and heating the material. As a non-limiting example, an auger may be disposed within the chute 218 and in communication with the gearbox 208. In such a non-limiting example, the auger may compress and move the material. In such an embodiment, the material is converted from its raw form to a form more easily extruded by the extruder 106.

In an embodiment, one or more fans 210 are disposed around the extruder 106. The one or more fans 210 may be directed at the material as it exits the extruder 106 (for example, to cool the material). In an embodiment, a fan 210 may be disposed on the chute 218 (for example, through a vent along the chute 218). In such an embodiment, the fan 210 may cool the material before exiting the extruder 106. The one or more fans 210 may be in communication with the computing device (for example, the computing device may instruct the fans 210 when to engage, disengage, or change RPM). In an embodiment, the one or more fans 210 are in electrical communication with the computing device. The machine may be equipped with sensors configured to evaluate characteristics (for example, temperature and plasticity) of the material (for example, before, during, and after extrusion). In such an embodiment, the computing device may be configured to adjust the one or more fans 210 based on characteristics of the extruded material. As a non-limiting example, if the extruded material is too cool as it is being layered on the build platform, the computing device may instruct the one or more fans 210 to decrease their RPM.

In an embodiment, a z-axis plate 214 is slidably coupled to z-axis rails 216. In one embodiment, the z-axis plate 214 may include a number of holes sized to accept at least the z-axis rails 216. In an embodiment, the z-axis plate 214 accepts a single z-axis rail 216. However, in another embodiment, the z-axis plate 214 accepts two or more z-axis rails 216. In an embodiment, a z-axis top plate 212 may accept the top end of the z-axis rails 216. The z-axis top plate 212 may be disposed between the compression head 102 and a vertical support 220. The vertical support 220 may be tubing or another support configured to hold up at least the compression head 102. The vertical support 220 may be attached to the base plate 410 and/or the table component 112.

In an embodiment, a z-axis motor 222 is disposed beneath the base plate 410. However, in an alternate embodiment, the z-axis motor 222 may be disposed on any portion of the machine 100 (for example, on the z-axis top plate 212). In an embodiment, the z-axis motor 222 is mechanically connected to a z-axis screw 224. The z-axis screw 224 is threaded and may be configured and sized to be accepted by the z-axis plate 214. In such an embodiment, the z-axis plate 214 may include a hole that is threaded in accordance with the threads of the z-axis screw 224. Further, in such an embodiment, the rotational motion imparted on the z-axis screw 224 by the z-axis motor 222 may cause the z-axis plate 214 to move along the z-axis. Thus, the z-axis motor 222 may move the entire compression head 102 along the z-axis.

Figure 3:
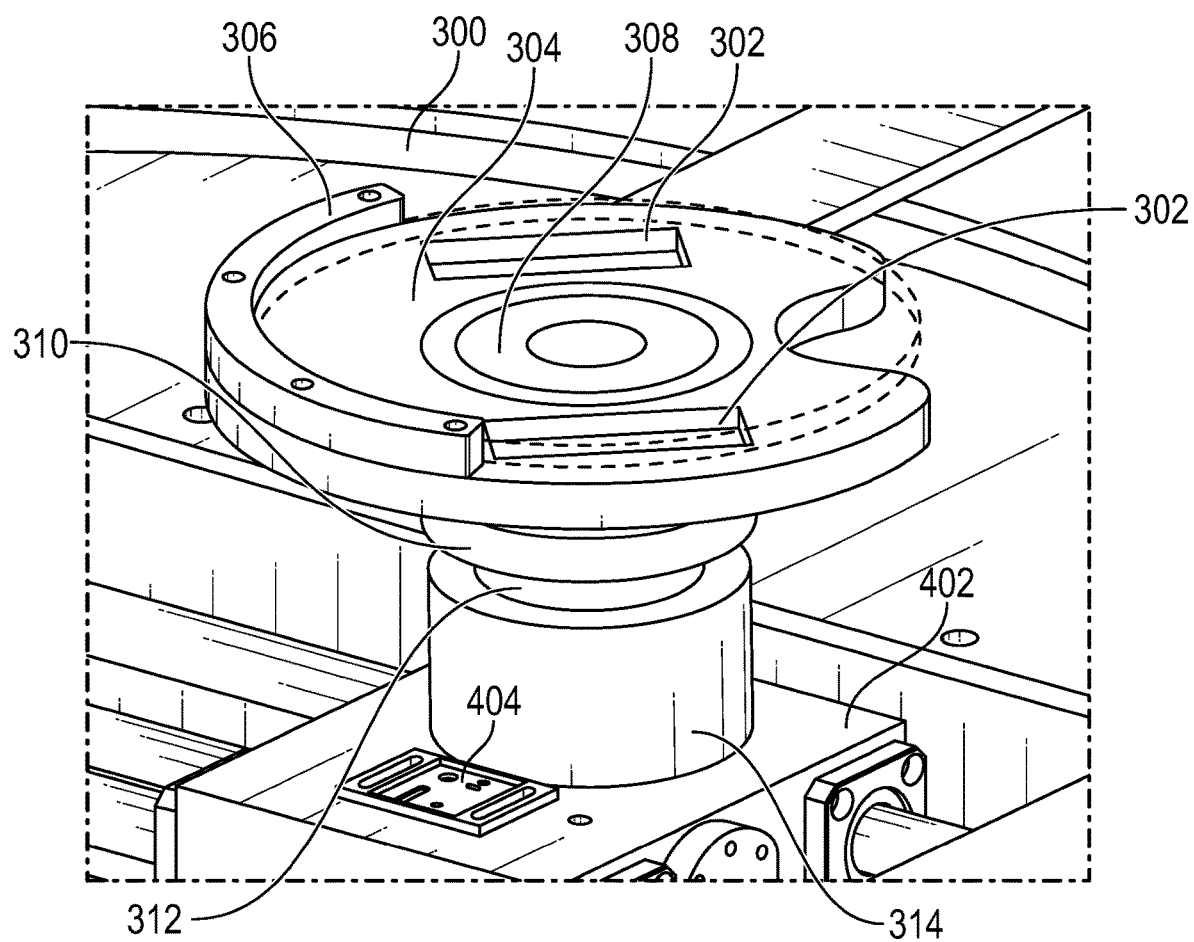
FIG. 3 illustrates a detailed front top side view of a build plate assembly of the machine, according to an embodiment.

Referring to FIG. 3, the machine 100 includes a build plate assembly 300. The build plate assembly 300 may include a plate holder 304. The plate holder 304 may be a disc configured and sized to accept a build plate. A plate holder top 306 may be disposed on the rim of the plate holder 304. As a non-limiting example, the plate holder top 306 may be configured to hold a build plate in position on the plate holder 304. In an embodiment, the plate holder 304 includes one or more heaters 302. The one or more heaters 302 may be disposed on the top surface of the plate holder 304. The one or more heaters 302 may be configured to apply heat to the project as it is being constructed (for example, indirectly by heating the build plate). In an embodiment, the one or more heaters 302 are in electrical communication with the computing device. The computing device may instruct the one or more heaters 302 to increase or decrease their heat output based on characteristics of the project and/or material.

In an embodiment, an electromagnet 308 is disposed in at least the center of the plate holder 304. An electromagnet adapter 310 may be disposed beneath the electromagnet 308. The electromagnet adapter 310 may be disposed between the electromagnet 308 and the spindle 312. In a further embodiment, a slip ring 314 may be disposed between the main plate 402 and the spindle 312. However, in alternate embodiments, the electromagnet 308, electromagnet adapter 310, spindle 312, and slip ring 314 may be configured in any orientation or order. The electromagnet 310 may in electrical communication with the computing device. The computing device may be configured to instruct the electromagnet 310 to engage or disengage based on whether the build plate is ready to be removed from the build plate holder 304.

Figure 4:
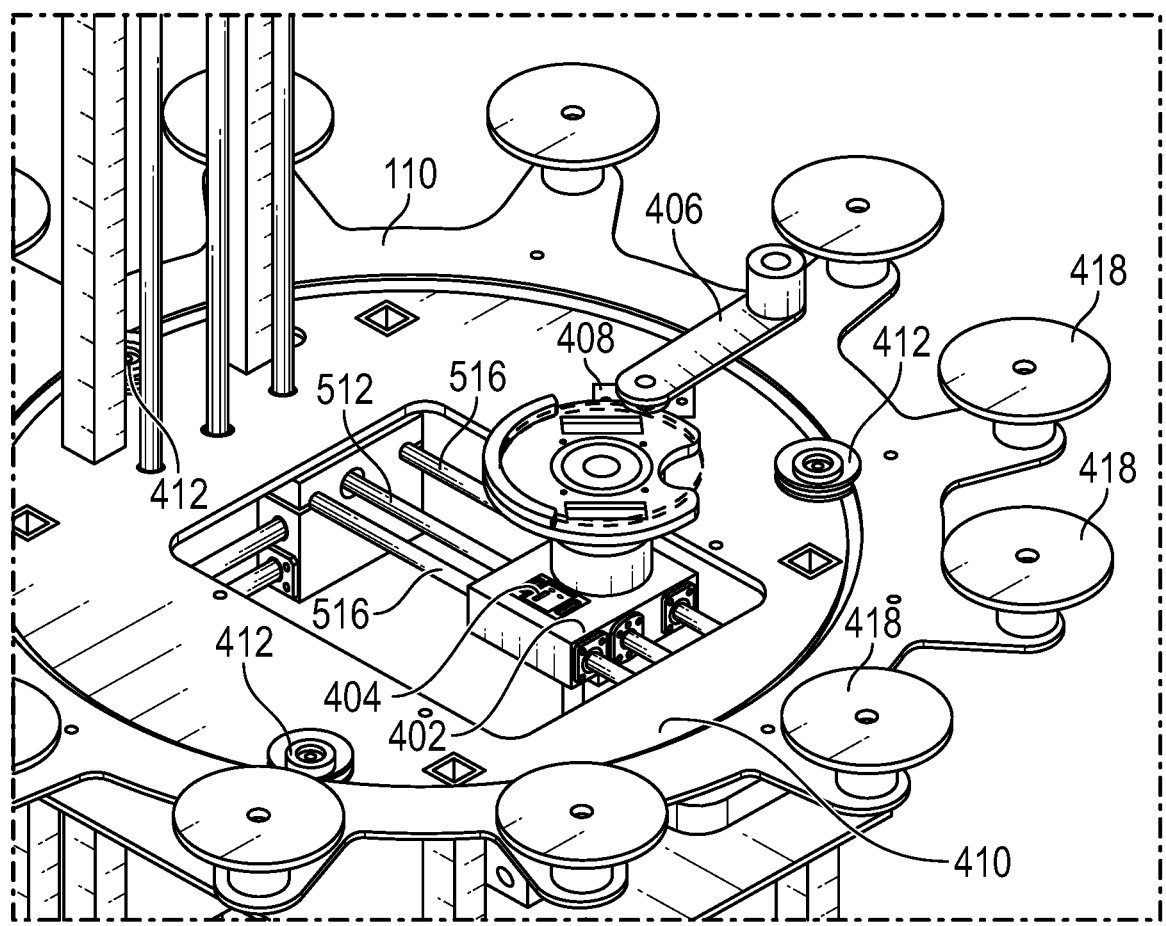
FIG. 4 illustrates a detailed front top side view of the machine with a base plate and a carousel, according to an embodiment.

Referring to FIG. 4, in an embodiment, the machine 100 includes a main plate 402 configured to accept the build plate assembly 300. In one embodiment, a hall sensor 404 is disposed on the top surface of the main plate 402. The hall sensor 404 may be utilized as a limit/home switch. In an embodiment, the rotary axis utilizes a home switch. The main plate 402 may be configured to move, with the assistance of motors, in at least one linear axes. In an embodiment, the hall sensor 404 and/or other sensors are in electrical communication with the computing device. These sensors may be utilized by the computing device to determine the coordinates, positions, or speeds of the build plate, other components of the machine 100, or the printed prosthetic.

In an embodiment, a carousel arm 406 may be configured to move a build plate from the build plate assembly 300 to the carousel 110. The carousel arm 406 may be attached to the base plate 410 (for example, via an arm support 408). One or more pulleys 412 may be disposed between the base plate 410 and the carousel 110. For example, one or more pulleys 412 may be attached to the outer most rim of the base plate 410 and/or the inner most rim of the carousel 110. In an embodiment, one or more pulleys 412 are in mechanical communication with one or more pulley motors 414. The pulley motor 414 may be configured to rotate the pulley 412, in turn rotating the carousel 110. In an embodiment, each pulley 412 includes a pulley motor 414. However, in another embodiment, only one of the pulleys 412 includes a pulley motor 414. In an embodiment, the pulley motor 414 is disposed beneath the base plate 410, such that the pulley motor 414 imparts rotational motion on the pulley 412, causing the carousel 110 to rotate. In an embodiment, the one or more pulley motors 414 may be in electrical communication with the computing device, enabling the computing device to determine when to rotate the carousel 110 (for example, when the next print is ready to begin).

In an embodiment, the carousel arm 406 may be in mechanical communication with an arm motor 420. The arm motor 420 may impart a rotational motion on the carousel arm 406, enabling the carousel arm 406 to move build plates between the carousel 110 and the build plate assembly 300.

Figure 5:
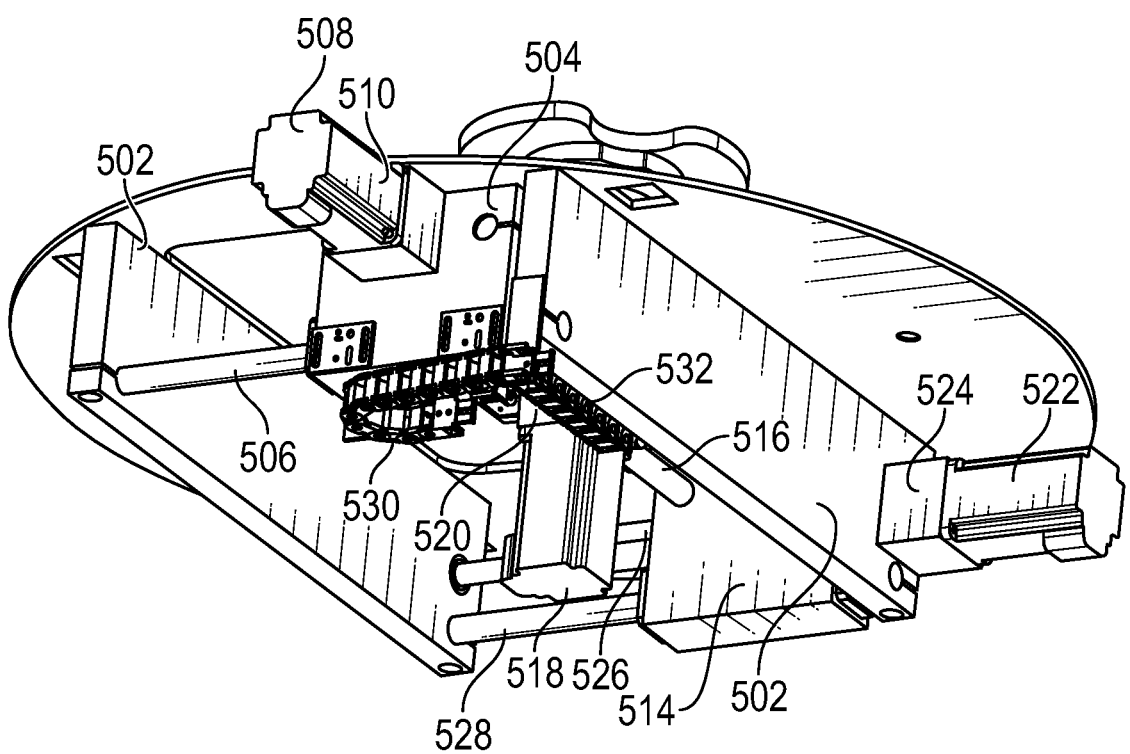
FIG. 5 illustrates a bottom front side perspective view of the machine, exhibiting one or more motors and rails, according to an embodiment.

Referring to FIG. 5, the machine includes one or more side plates 502. The side plates 502 may be attached to the bottom surface of the base plate 410. For example, the side plates 502 may be parallel and some distance apart. In an embodiment, the side plates 502 are attached to the table component 112. In an embodiment, one or more x-axis rails 506 run between the side plates 502. In an embodiment, a y-axis plate 504 is attached to at least one x-axis rail 506. As a non-limiting example, the y plate 504 may include one or more holes configured and sized to accept an x-axis rail 506. They plate 504 may accept a y motor mount 510, where they motor mount 510 is attached to a y-axis motor 508. The y-axis motor 508 may be in mechanical communication with a y-axis screw 512. The y-axis screw 512 may be a long cylindrical member (at least partially threaded) disposed between the y plate 504 and the end plate 514. In an embodiment, the y-axis screw 512 is disposed through the main plate 402. For example, the main plate 402 may include a y-axis screw hole configured and sized to accept the y-axis screw 512. Further, the y-axis screw hole may be threaded such that rotation of the y-axis screw 512 by the y-axis motor moves the main plate 402 along the y-axis.

In an embodiment, one or more y-axis rails 516 run from the y plate 504 to the end plate 514. The one or more y-axis rails 516 may be slidably attached to the main plate 402. For example, the main plate 402 may include one or more y-axis holes sized and configured to accept one or more y-axis rails 516. Further, the y-axis rails 516 may maintain the main plate 402 in position while also enabling the main plate 402 to slide along the y-axis rails 516.

In an embodiment, a rotary motor 518 is disposed on the underside of the main plate 402. However, in alternate embodiments, the rotary motor 518 may be disposed atop the main plate 402. In another embodiment, a rotary motor mount 520 is disposed between the main plate 402 and the rotary motor 518. The rotary motor 518 is configured to rotate the build plate (for example, by rotating components of the build plate assembly 300, such as the build plate holder 304).

In an embodiment, the machine 100 includes an x-axis motor 522. In such an embodiment, the x-axis motor 522 may be disposed on the side plate 502 (for example, via an x-axis motor mount 524). However, in alternate embodiments, the x-axis motor 522 may be disposed on any portion of the machine 100. The x-axis motor 522 may be in mechanical communication with an x-axis screw 526. The x-axis screw 526 may run between the two side plates 502 and may be threaded. In an embodiment, the end plate 514 includes one or more holes sized and configured to accept at least an x-axis rail 528 and the x-axis screw 526. The hole for the x-axis screw 526 may be threaded in accordance with the threads along the x-axis screw 526, enabling the x-axis motor 522 to move the end plate along the x-axis screw 526 and x-axis rail 528. In an embodiment, the x-axis motion of the end plate 514 imparts a synonymous x-axis motion in the main plate 402. Thus, the x-axis motor 522 may indirectly drive the main plate 402 along the x-axis. Further, the y-axis motor 508 may drive the main plate 402 along the y-axis. Further, the rotary motor 518 may drive the build plate to rotate about the rotary axis (in one example, in the same plane as the x and y axis)

Successively, a printed object may be formed on the build plate through motion that is controlled by the plurality of linear axes and the rotary axis. In one case, the motion of the build plate may be controlled by 3 linear axes and 1 rotary axis. In another case, the motion of the build plate may be controlled by 2 linear axes and 1 rotary axis. It should be noted using a combination of 3 linear axes and a rotary axis, the granular polycarbonate material may be placed in a precise position on the build plate. In one embodiment, each linear axis may consist of at least two round linear rails with at least four bearings. Thus, the build plate motion may be driven by any combination of: the x-axis motor 522, the y-axis motor 508, and the rotary motor 518.

In an embodiment, the machine 100 includes an x-axis cable track 530 and/or a y-axis cable track 532. The x-axis cable track 530 may be attached to the side plate 502 and the y plate 504. The y-axis cable track 532 may be attached to the side plate 502 and the main plate 402. However, the cable tracks 530-532 may be attached to any components of the machine 100. In an embodiment, the cable tracks 530-532 may be utilized to contain and carry cables associated with moving parts (for example, to prevent tangled wires or undue stress on cables).

Further, the motion of the main plate 402 may be achieved through a ball screw and a nut which are direct driven by a stepper motor with a rotary encoder. Further, the rotary axis may be a bearing supported shaft that is directly driven by a stepper motor with an encoder. Further, the extruder (i.e., custom shaped tip) 106 may be mounted on a vertical linear axis. Further, a part being printed may be printed on a metal plate (for example, the build plate) that sits on a top of the build plate assembly 300 or print surface 108 (for example, rotary table) which has an electromagnet 308 and two heaters 302 built into it, as shown in FIG. 3. It should be noted that a "slotted" end may be on axis at all times in order to form a 4 mm thick wall of the part in a single pass. That is, without remaining on axis, printing may occur on an angle, and out of center. In an embodiment, the extruder 106 includes an adjustable tip (for example, the tip's diameter and angle may be adjusted).

Figure 6:
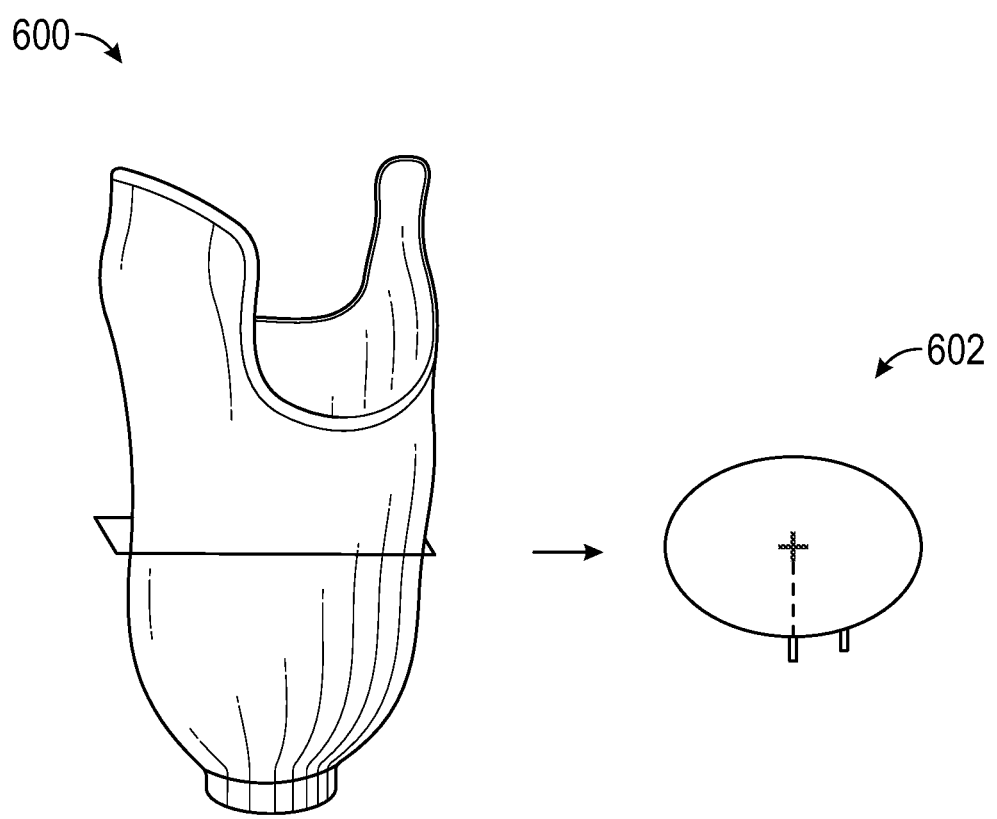
FIG. 6 illustrates an exemplary scenario of a prosthetic limb created using the machine, according to an embodiment.

Successively, the build plate with the printed object (i.e., attached model) may be placed on the outer carousel 110. The outer carousel 110 may be rotated and a new build plate may be retrieved. Thereafter, the new build plate may be placed on the build plate assembly 108 when the machine 100 is ready for the next print. It should be noted that in order to achieve unprecedented speeds, the build plate may be rotated and a large quantity of material may be deposited due to the "ribbon" deposition. In an example, the ribbon may be deposited on center at all times to enable an accurate build, as shown in FIG. 6. FIG. 6 illustrates an example of a prosthetic 600. Thereafter, the center of each slice 602 may be calculated and the linear axes may move appropriately during rotation. Thus, the result of the process may be rapidly producing a consistent wall thickness socket very quickly.

In an embodiment, the various motors are in electrical communication with the computing device. The computing device includes the software necessary to splice the design of the desired prosthetic and the software necessary to drive each motor in accordance with the design. Thus, the computing device is configured to execute instructions that cause the machine 100 to heat and compress the material to an appropriate level, to cause the gearbox 208 to extrude the proper amount of material, to cause the x-axis motor 522, y-axis motor 508, z-axis motor 222, and rotary motor 518 to move the main plate 402 such that the extruder 106 extrudes the material in accordance with the prosthetic design, to cause the carousel arm 406 to remove the finished prosthetic, to cause the carousel 110 to rotate, and to cause the machine 100 to begin manufacture of the next desired prosthetic.

In one embodiment, both linear axes may be rotated. This rotation may be necessary to maintain the rotary axis on center, while the center of the slot changes.

In an embodiment, the combination of a slotted end and printing on three moving axes may result in an accurate, relatively fast-moving prosthetics formation apparatus.

It will be apparent to one skilled in the art that the granules may be a plastic material. In one case, 3 mm Polyethylene Terephthalate Glycol (PETG) granules may be used. Further, a blend of thermoplastic elastomer (TPE) and thermoplastic polyurethane (TPU) granules may be used. Further, the extruded plastic may have a shape of a flat ribbon 4 mm wide, without departing from the scope of the disclosure. In an embodiment, the granules may be compressed, and form a ribbon. The ribbon may be extruded. In an exemplary embodiment, the ribbon may be extruded at measurements of 1 mm×5 mm, though any other suitable size, such as 1-10 mm×1-30 mm, are contemplated by the invention.

Figure 7:
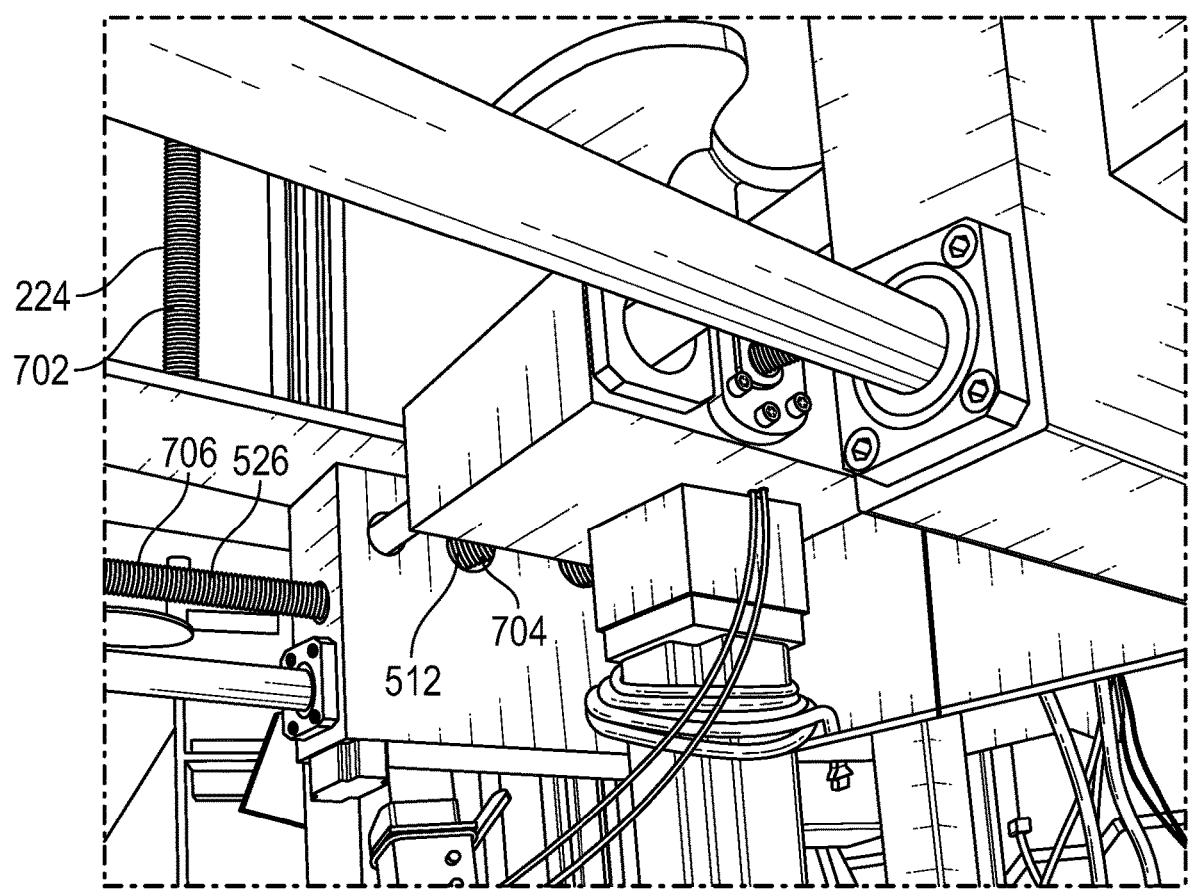
FIG. 7 illustrates a detailed side bottom front perspective view of a configuration of the rotary axis and two related horizontal linear axes.

FIG. 7 illustrates a configuration of the rotary axis and two related horizontal linear axes. In this embodiment, the vertical motor drives the rotary axis. In an embodiment, the z-axis screw 224 includes a z-axis thread pitch 702. The y-axis screw 512 may include a y-axis thread pitch 704. Further, the x-axis screw 526 may include a x-axis thread pitch 706. Each of the aforementioned thread pitches may be the same thread pitch or different thread pitches. In an embodiment, each of the main plate 402, end plate 514, and z-axis plate 214, may include holes configured to interface with at least one of the thread pitches 702-706. In an embodiment, rotation of each of the screws may impart motion on the corresponding plate.

Figure 8:
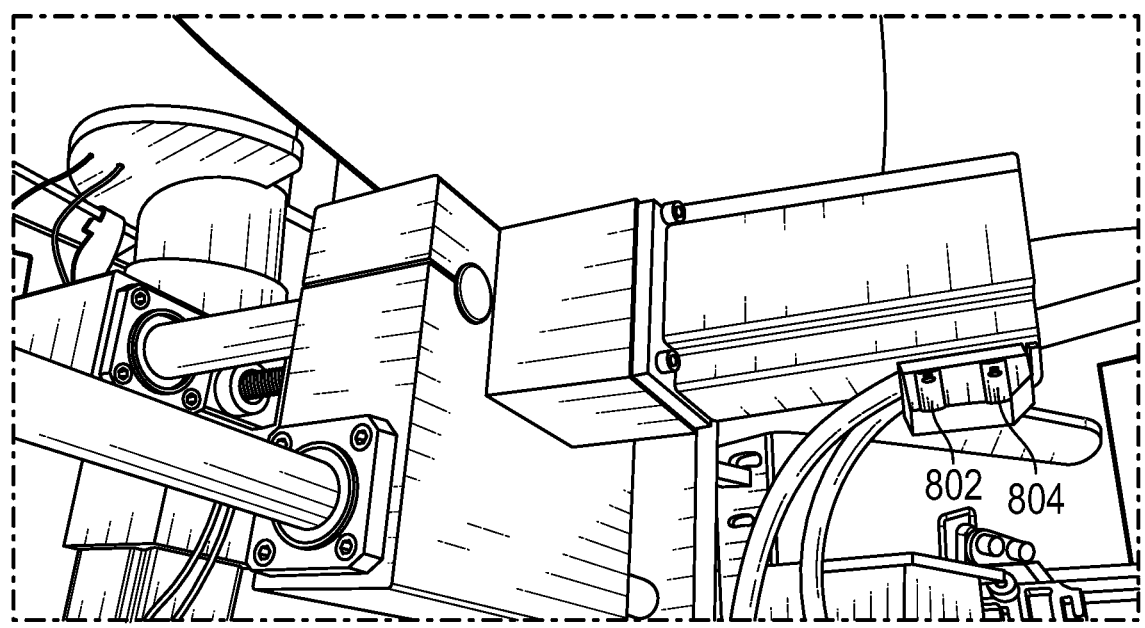
FIG. 8 illustrates a detailed side bottom perspective view of a configuration of the rotary axis and two related horizontal linear axes, with the horizontal motor driving one of the linear axes.

FIG. 8 illustrates a configuration of the rotary axis and two related horizontal linear axes, with the horizontal motor driving one of the linear axes. In an embodiment, one or more of the motors includes a power input 802 and an information input 804. The power input 802 may be in communication with the computing device and may be configured to deliver power to the motor. The information input 804 may be in communication with the computing device and may facilitate instructions to the motor (for example, instructing the RPM of the motor).

Figure 9:
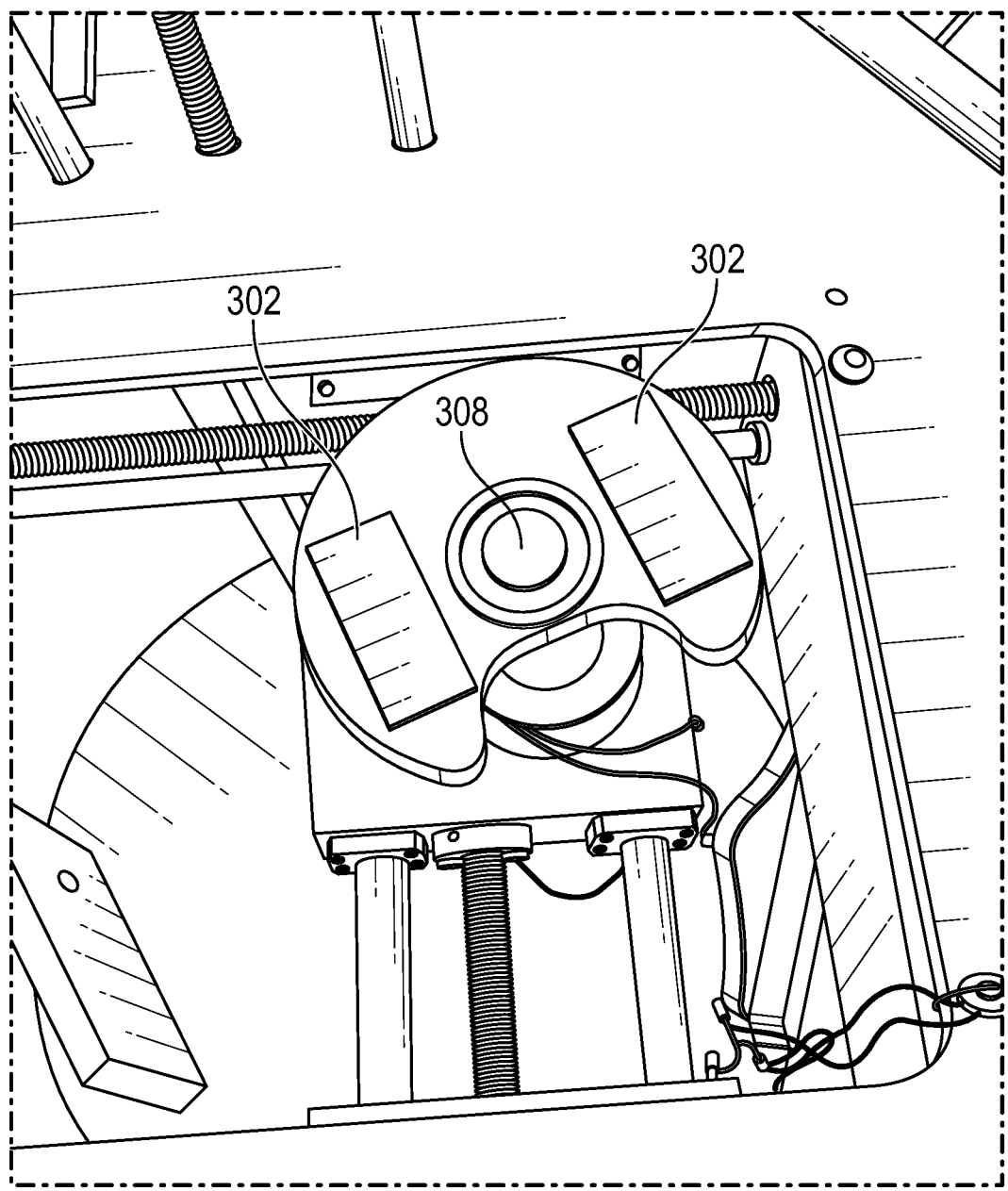
FIG. 9 illustrates a top view of the rotary axis and the two related horizontal axes, with the heated magnetic rotary platform clearly visible.

FIG. 9 illustrates a top view of the rotary axis and the two related horizontal axes, with the heated magnetic rotary platform clearly visible. In an embodiment, the plate holder 304 comprises one or more heaters 302 and an electromagnet 308. The one or more heaters 302 and the electromagnet 308 may be in electrical communication with the computing device. The electromagnet 308, when engaged, may be configured to attract the build plate 418. The heater 302 may be configured to heat the build plate 418, indirectly heating the prosthetic before, during, and/or after printing. The computing device may instruct the electromagnet 308 to disengage when the printing is complete and/or when the carousel arm 406 attempts to remove the build plate 418.

Figure 10:
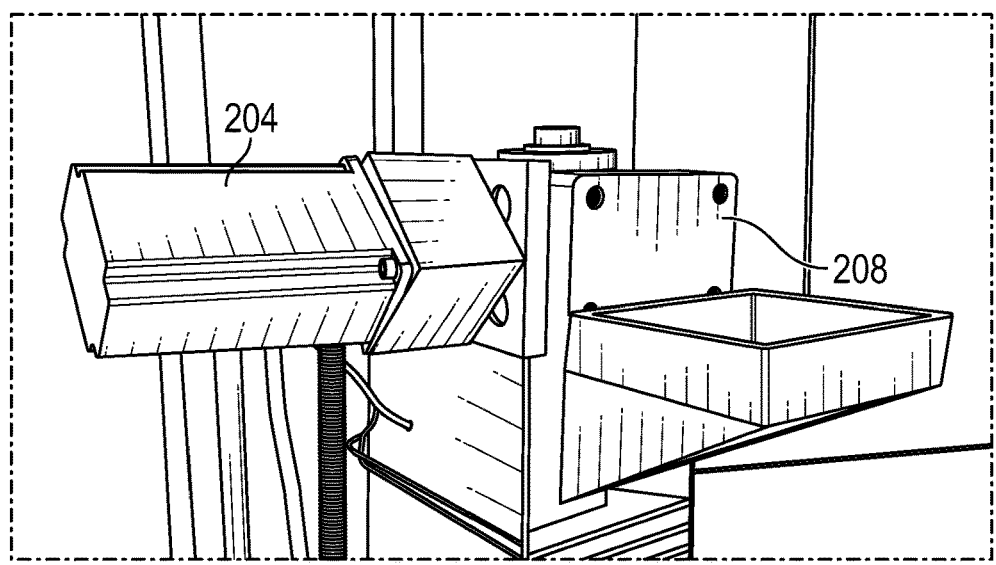
FIG. 10 illustrates a detailed side front perspective view of a motor connected to the gearbox of the printhead.

FIG. 10 illustrates the feed motor 204 connected to the gearbox 208 of the printhead.

Figure 11:
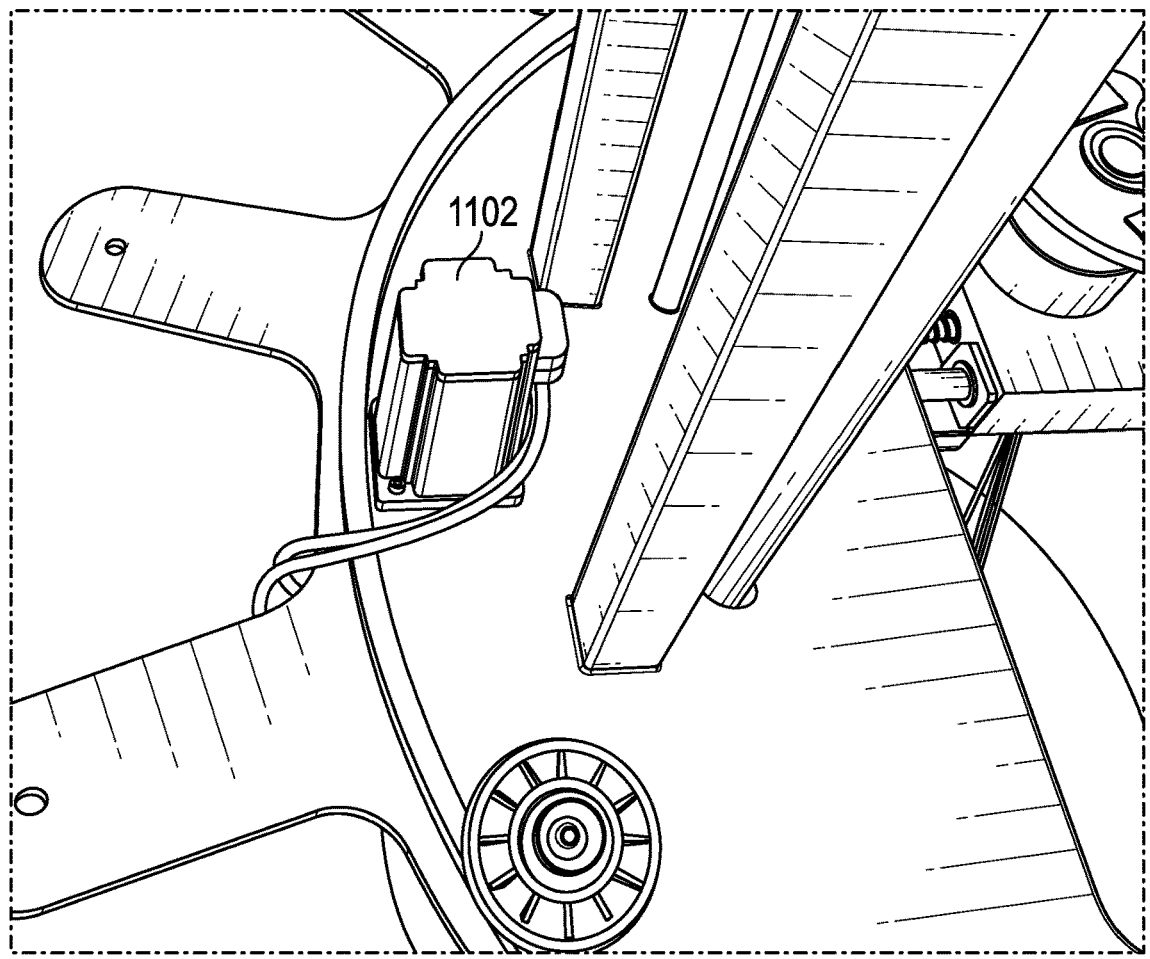
FIG. 11 illustrates a detailed view of a motor driving the carousel.

FIG. 11 illustrates a carousel motor 1102 driving the carousel 110. The carousel motor 1102 may be rotationally attached to one or more pulleys 412. However, in an alternate embodiment, the carousel motor 1102 rotates the carousel 110 in conjunction with the pulley motor 414.

Figure 12:
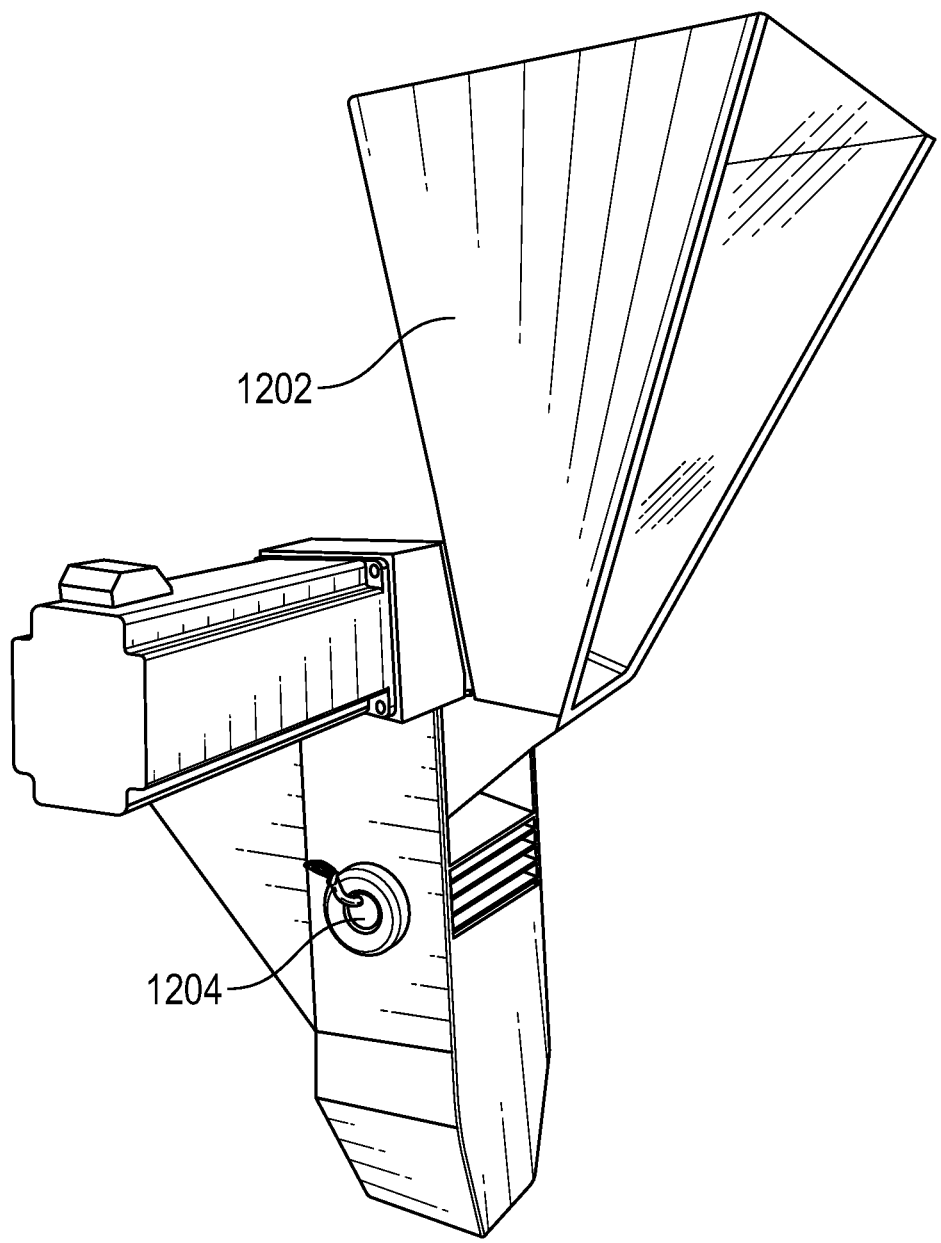
FIG. 12 illustrates a front side perspective view of an assembled printhead accompanied with a granule hopper.

FIG. 12 illustrates an assembled printhead, with a granule hopper 1202. In such an embodiment, the hopper 1202 may be utilized in conjunction with or instead of the cartridge 104. A chute fan 1204 may be disposed on the chute (for example, on a chute fan vent). The chute fan 1204 may be configured to cool the material before extrusion.

Figure 13:
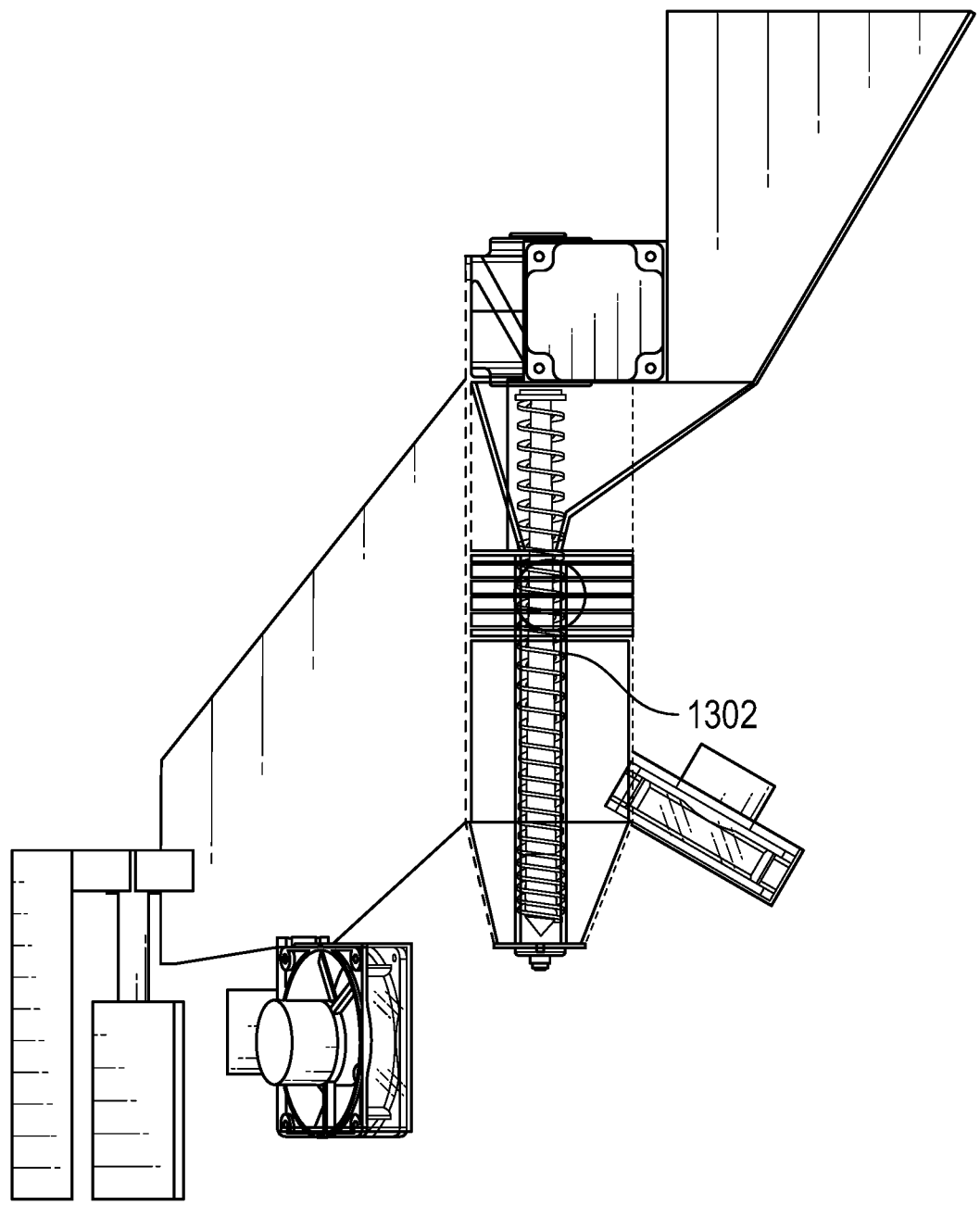
FIG. 13 illustrates a side view of an embodiment of the machine including a motor, a gearbox, and an auger.

FIG. 13 illustrates an embodiment of the machine 100 having an auger 1302. The auger 1302 may be in rotational mechanical communication with the gearbox 208 and/or feed motor 204. The auger 1302 may be configured to drive the material from the cartridge 104 and/or hopper 1202 to the extruder 106. The auger 1302 may be disposed vertically though the center of the chute 218. In an embodiment, the chute 218 may be sized to accept the auger 1302. The auger 1302 may include threads sized with the same diameter as the chute 218, such that the auger 1302 is snug in the chute 218. The auger 1302 may also include threads with a varying frequency of twists. For example, the auger 1302 may include a higher density of twists towards the bottom section of the auger. In such a non-limiting example, a varying frequency of twists along the auger 1302 may be configured to gradually compress the material. In an embodiment, the speed of the feed motor 204 and/or gear ratio in the gearbox 208 dictates the rate at which material is extruded by the extruder 106. In such an embodiment, the feed motor 204 and/or gearbox 208 are in electrical communication with the computing device. Thus, the computing device may control the rate at which material is extruded.

While this invention has been described in conjunction with the embodiments outlined above, many alternatives, modifications and variations will be apparent to those skilled in the art upon reading the foregoing disclosure. Accordingly, the embodiments of the invention, as set forth above, are intended to be illustrative, not limiting. Various changes may be made without departing from the spirit and scope of the invention.

What is claimed is:

1. An additive manufacturing apparatus comprising:
   a cartridge comprising a top opening and a bottom opening, the cartridge configured to accept a material,
      wherein the cartridge is tapered from the top opening to the bottom opening;
   an extruder configured to extrude the material;
   a chute disposed between the cartridge and the extruder;
   a z-axis plate attached to the cartridge and the extruder;
   a z-axis motor configured to move the z-axis plate in a z-axis;
   a main plate having a plate holder configured to accept a build plate,
      wherein the build plate is configured to accept the material from the extruder;
   a carousel configured to revolve about the main plate,
      wherein the carousel is configured to receive the build plate;
   a carousel arm configured to move the build plate between the carousel and the plate holder:
   at least one pulley disposed between a base plate and the carousel,
      wherein the at least one pulley enables rotational motion of the carousel;
   a pulley motor disposed beneath the base plate,
      wherein the pulley motor is in mechanical communication with the at least one pulley;
   a y-axis motor configured to move the main plate in a y-axis; a rotary motor configured to move the plate holder in a rotary axis; and a computing device having a processor and a memory, the computing device in electrical communication with at least the z-axis motor, the y-axis motor, and the rotary motor, wherein the memory contains a design and a computer-readable instruction for printing the design, and wherein the computing device is configured to drive the z-axis motor, the y-axis motor, and the rotary motor in accordance with the computer-readable instruction for printing the design.

2. The apparatus of claim 1 further comprising one or more fans disposed proximate to the extruder.

3. The apparatus of claim 1 further comprising one or more heaters partially disposed within the plate holder.

4. The apparatus of claim 1 further comprising an electromagnet partially disposed within the plate holder.

5. The apparatus of claim 1 further comprising an electromagnet adapter and a spindle, wherein the electromagnet and the spindle are disposed between the rotary motor and the plate holder.

6. The apparatus of claim 1 further comprising a z-axis screw in mechanical rotational communication with the z-axis motor, wherein the z-axis screw is at least partially threaded, and wherein the z-axis plate comprises a z-axis screw hole having a z-axis thread pattern configured to accept the z-axis screw.

7. The apparatus of claim 1 further comprising a y-axis screw in mechanical rotational communication with the y-axis motor, wherein the y-axis screw is at least partially threaded, and wherein the y-axis plate comprises a y-axis screw hole having a y-axis thread pattern configured to accept the y-axis screw.

8. The apparatus of claim 1 further comprising a hall sensor disposed on the main plate.

9. The apparatus of claim 1 further comprising one or more y-axis rails disposed between the y-axis plate and an end plate, wherein the main plate is slidably attached to the one or more y-axis rails.

10. The apparatus of claim 9 further comprising:

an x-axis motor configured to move the end plate in an x-axis, wherein the main plate is configured to move in the x-axis contemporaneously with the end plate; and an x-axis screw in mechanical rotational communication with the x-axis motor, wherein the x-axis screw is at least partially threaded, and wherein the end plate comprises a x-axis screw hole having a x-axis thread pattern configured to accept the x-axis screw.

11. The apparatus of claim 1 wherein the cartridge comprises a front window.

12. The apparatus of claim 1 further comprising a feed motor and a gearbox, the feed motor and the gearbox configured to move the material from the cartridge to the extruder.

13. The apparatus of claim 1 wherein the extruder is configured to extrude the material in a ribbon.

14. The apparatus of claim 1 further comprising an auger disposed within the chute, the auger configured to drive material from the cartridge to the extruder.

15. The apparatus of claim 13, wherein the ribbon is 4 mm wide.

* * * * *